United States Patent
Schoepgens et al.

(10) Patent No.: US 10,322,071 B2
(45) Date of Patent: *Jun. 18, 2019

(54) HAIR DYE

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA, Duesseldorf (DE)

(*) Notice: Subject to any disclaimer, the term of this patent is extended or adjusted under 35 U.S.C. 154(b) by 1 day.

This patent is subject to a terminal disclaimer.

(21) Appl. No.: 15/826,683

(22) Filed: Nov. 30, 2017

(65) Prior Publication Data
US 2018/0168941 A1 Jun. 21, 2018

(30) Foreign Application Priority Data

Dec. 19, 2016 (DE) .................. 10 2016 225 382

(51) Int. Cl.
*A61Q 5/10* (2006.01)
*A61K 8/04* (2006.01)
*A61K 8/41* (2006.01)
*A61K 8/46* (2006.01)
*A61K 8/81* (2006.01)
*A61K 8/37* (2006.01)
*A61K 8/42* (2006.01)
*A61K 8/86* (2006.01)

(52) U.S. Cl.
CPC .............. *A61K 8/042* (2013.01); *A61K 8/375* (2013.01); *A61K 8/41* (2013.01); *A61K 8/42* (2013.01); *A61K 8/463* (2013.01); *A61K 8/8147* (2013.01); *A61K 8/8152* (2013.01); *A61K 8/86* (2013.01); *A61Q 5/10* (2013.01); *A61K 2800/30* (2013.01); *A61K 2800/4324* (2013.01); *A61K 2800/882* (2013.01)

(58) Field of Classification Search
CPC ... A61Q 5/10; A61K 8/41; A61K 8/42; A61K 8/463; A61K 8/375; A61K 2800/882; A61K 2800/4324
See application file for complete search history.

(56) References Cited

U.S. PATENT DOCUMENTS

2001/0042276 A1   11/2001 Kawasoe et al.
2012/0285479 A1*  11/2012 Zirwen ............... A61K 8/046
                                                         132/208

FOREIGN PATENT DOCUMENTS

JP          2001151647 A     6/2001

OTHER PUBLICATIONS

Intellectual Property Office, GB Search Report issued in Application No. GB1719922.5, dated Aug. 23, 2018.

* cited by examiner

Primary Examiner — Eisa B Elhilo
(74) Attorney, Agent, or Firm — Lorenz & Kopf, LLP

(57) ABSTRACT

The subject matter of the present disclosure relates to agents for oxidative hair dyeing, containing from about 70-about 95 wt. % water, oxidation dye precursor(s), alkalizing agents, from about 0.1-about 2 wt. % anionic, zwitterionic or amphoteric tenside, from about 0.1-about 1.5 wt. % sodium polyacrylate, wherein only small quantities, if any, of linear, saturated alkanols with two or three hydroxy groups and from 2 to 8 carbon atoms are contained in the alkyl group, also no saturated or unsaturated non-alkoxylated alkanols with a hydroxy group and from 1 to about 50 carbon atoms in the alk(en)yl group, no saturated or unsaturated alkanecarboxylic acids with from 1 to about 50 carbon atoms and no oxidants are contained in the agent.

20 Claims, No Drawings

HAIR DYE

CROSS-REFERENCE TO RELATED APPLICATION

This application claims priority to German Patent Application No. 10 2016 225 382.4, filed Dec. 19, 2016, which is incorporated herein by reference in its entirety.

TECHNICAL FIELD

The present application relates to an oxidative hair dye, a kit, comprising said dye and a hair dyeing method employing said hair dye.

BACKGROUND

To achieve permanent, intense colors with corresponding fastness properties, so-called oxidative dyes are used. Said dyes usually contain oxidative dye precursors, so-called developer components and coupler components. The developer components join together or couple with one or more coupler components to form, under the influence of oxidants or atmospheric oxygen, the actual dyes per se. Indeed, the oxidative dyes are exemplified by outstanding, long-lasting color results. To achieve natural-looking colors, however, a mixture from a larger number of oxidative dye precursors (ODP) must normally be used; in many cases, partially-oxidizing dyes are still used to create the tinting effect.

Most of the oxidative dyes used for stabilizing the dye precursors during storage and to accelerate the reaction during oxidative application have an alkali pH value, which is set with alkalizing agents such as alkanolamines, ammonia or inorganic bases.

To produce the dye, the alkali coloring component is usually mixed with a hydrous hydrogen peroxide solution to form a homogeneous creme or a homogeneous gel, and then applied immediately to the hair to be dyed. This dye mixture remains on the hair for a period of from about 5 to about 60 minutes, until the oxidative formation of the dye on the hair is complete. The dye mixture is then washed out.

The aforementioned oxidative precursors (OPC) and alkalizing agents are usually worked into the hair in a cosmetically suitable carrier, such as a creme, for example. The carrier guarantees a homogeneous distribution and an adequate dwell time of the hair dye on the hair.

The disadvantage is the complex manufacture of such a creme. The fusing of the fat components and the emulsification process requires a high amount of energy. The subsequent cooling process consumes large quantities of cooling water.

A further disadvantage is that a creme has to be packaged in a relatively complex manner. Due to their higher viscosity, cremes are incapable of flowing and cannot be transferred from a storage bottle into the application bottle, in which the hydrogen peroxide solution has already been placed, simply by tipping. Instead, the alkali dye cremes are packed primarily in flexible aluminum tubes, packaging material with high energy and raw material consumption.

A higher viscosity of the dye creme is a further disadvantage in terms of producing the application mixture. The alkali dye creme is mixed with the developer preparation by hand. The most homogeneous application mixture possible is required to achieve an effective color result. It must be possible to produce said mixture within the shortest possible time. This is because the oxidation dye precursors start to react as soon as they come into contact with the hydrogen peroxide and the atmospheric oxygen. The fastest possible mixture is achieved most readily if dye creme and developer preparation are as fluid as possible. Conversely, the application mixture itself should be more viscose so that it remains on the hair without dripping.

BRIEF SUMMARY

Agents for oxidative hair dyeing, kits-of-parts including the agents, and methods for oxidative hair dyeing using the agent are provided herein. In an embodiment, an agent for oxidative hair dyeing includes water, at least one oxidation dye precursor, at least one alkalizing agent, at least one tenside, sodium polyacrylate, and optionally at least one linear, saturated alkanol with two or three hydroxy groups and from about 2 to about 8 carbon atoms in the alkyl group. The at least one tenside is selected from anionic, zwitterionic and amphoteric tensides, as well as mixtures thereof. Relative to the weight of the agent in each case, the agent includes the water in an amount of from about 70 to about 95 wt. %, the at least one tenside in a total quantity of from about 0.1-about 2 wt. %, the sodium polyacrylate in a total quantity of from about 0.1-about 1.5 wt. %, and at least one linear, saturated alkanol with two or three hydroxy groups and from about 2 to about 8 carbon atoms in the alkyl group in a total quantity of from 0-about 3 wt. %. No saturated or unsaturated non-alkoxylated alkanols with a hydroxy group and from about 1 to about 50 carbon atoms in the alk(en)yl group are included in the agent. No saturated or unsaturated alkanecarboxylic acids with from about 1 to about 50 carbon atoms are included in the agent. No oxidants are included in the agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure addressed the problem of providing an oxidative hair dye, which can be produced under the most cost-effective and sustainable conditions possible. The present disclosure also addressed the problem of providing an oxidative hair dye, which can be packaged under the most cost-effective and sustainable conditions possible. The present disclosure also addressed the problem of providing an oxidative hair dye, which is simple to blend and apply.

Said problems are solved by an agent for oxidative hair dye containing the following, in each case relative to its weight:

from about 70 to about 95 wt. % water,
at least one oxidation dye precursor,
at least one alkalizing agent,
at least one tenside, selected from anionic, zwitterionic and amphoteric tensides, as well as mixtures thereof, in a total quantity of from about 0.1-about 2 wt. %,
Sodium polyacrylate in a total quantity of from about 0.1-about 1.5 wt. %, preferably from about 0.5-about 1.3 wt. %, more preferably from about 0.8-about 11 wt. %, preferably with an average molecular weight Mw in the range from about 1,000,000 to about 20,000,000 Dalton, preferably from about 6,000,000 to about 15,000,000 Dalton, at least one linear, saturated alkanol with two or three hydroxy groups and from 2 to 8 carbon atoms in the alkyl group in a total quantity of from about 0-about 3 wt. %, wherein no saturated or unsaturated non-alkoxylated alkanols with a hydroxy group and from 1 to 50 carbon atoms in the alk(en)yl group and no saturated or unsaturated alkanecarboxylic acids with from 1 to 50 carbon atoms, and no oxidants are included in the agent.

The agent as contemplated herein constitutes the alkali dye component of an oxidative hair dye. This is usually mixed immediately before application with a hydrous hydrogen peroxide preparation and then applied to the hair to be dyed. Until mixed with the hydrous hydrogen peroxide preparation, the agent as contemplated herein contains no oxidants.

Water Content

The agent as contemplated herein contains, in each case relative to its weight, from about 70-about 95 wt. % water, preferably from about 78-about 91 wt. % water.

Alkalizing Agent

The agent as contemplated herein contains at least one alkalizing agent. The alkalizing agent preferred as contemplated herein for setting the preferred pH value is selected from the group comprising ammonium hydroxide, basic amino acids, alkali hydroxides, alkanolamines, alkali metal meta silicates, alkali phosphates and alkali hydrogen phosphates, as well as the mixtures thereof. Lithium, sodium and potassium, more particularly sodium or potassium are preferably used as alkali metal ions.

The basic amino acids that can be used as alkalizing agents are preferably selected from the group of L-arginine, D-arginine, D,L-arginine, L-lysine, D-lysine, D,L-lysine, L-arginine, D-arginine, D,L-arginine, are more preferably used as alkalizing agents as contemplated herein.

The alkali hydroxides that can be used as alkalizing agents are preferably selected from sodium hydroxide and potassium hydroxide.

The alkanolamines usable as alkalization agents are preferably selected from primary amines with a $C_2$-$C_6$-alkyl base body having at least one hydroxyl group. More preferred alkanolamines are selected from the group comprising 2-aminoethan-1-ol (monoethanolamine), 3-aminopropan-1-ol, 4-amino-butan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Most preferred alkanolamines as contemplated herein are selected from the group of 2-aminoethan-1-ol, 2-amino-2-methylpropan-1-ol and 2-amino-2-methyl-propan-1,3-diol.

A most preferred alkalizing agent as contemplated herein is monoethanolamine (2-aminoethan-1-ol). To achieve the most odorless dye method possible and to optimize the color fastness properties of the dye, monoethanolamine is contained in a total quantity of from about 0.2-about 10 wt. %, preferably from about 0.5-about 8 wt. %, more preferably from about 1 to about 6 wt. % and most preferably from about 2 to about 4 wt. %—relative to the weight of the dye as contemplated herein.

In addition to and/or instead of monoethanolamine, other preferred dyes as contemplated herein are ammonium hydroxide, i.e. ammonia in the form of its hydrous solution. Suitable hydrous ammonia solutions are from about 10 to about 35 percentage solutions (calculated in vol. %.) 100 g of hydrous ammonia solution with 25 vol. % $NH_3$ contain approx. 50 g of ammonia. Ammonia is preferably used in the form of a from about 20 to about 30 vol. % solution, most preferably in the form of a 25 vol. % solution.

In a most preferred embodiment, the dye as contemplated herein contains ammonium hydroxide in a quantity of from about 0.2 to about 6 wt. %, preferably from about 0.4 to about 5 wt. %, more preferably from about 1.0 to about 3 wt. % and most preferably from about 0.3 to about 1.5 wt. %, relative to the weight of the dye as contemplated herein.

Other alkalizing agents such as potassium hydroxide and sodium hydroxide can also be contained, preferably in a total quantity of from about 0.05 to about 1.5 wt. %, most preferably from about 0.1 to about 0.6 wt. %, in each case relative to the weight of the dye as contemplated herein.

In another most preferred embodiment, the dye as contemplated herein contains at least one alkalizing agent in a total quantity of from about 0.02-about 0.4 mol/100 g, preferably from about 0.05-about 0.3 mol/100 g, in each case in mol of alkalizing agents per 100 grams of agent as contemplated herein.

Preferred agents as contemplated herein are exemplified by a pH value in the range of from about 8-about 12, preferably from about 9-about 11.5, more preferably from about 9.5-about 10.5, in each case measured at 20° C.

Anionic Tenside, Zwitterionic Tenside or Amphoteric Tenside

The agent as contemplated herein contains, relative to its weight, at least one tenside, selected from anionic, zwitterionic r amphoteric tensides, as well as mixtures thereof, in a total quantity of from about 0.1-about 2 wt. %, preferably from about 0.3-about 1.5 wt. %, and most preferably from about 0.5-about 1.2 wt. %, in each case relative to the weight of said agent.

Tensides and emulsifiers according to the present disclosure are amphiphilic (bi-functional) compounds, which includes at least one hydrophobic and at least one hydrophilic molecular part.

According to the present disclosure, saturated and unsaturated alkan-1-oles having at least 4 carbon atoms in the alk(en)yl radical, alkanecarboxylic acids having at least 4 carbon atoms in the alk(en)yl radical and glyceryl fatty acid mono and diesters having at least 4 carbon atoms in the fatty acid radical are not considered tensides.

The hydrophobic radical is preferably a hydrocarbon chain with from 8-30 carbon atoms, which can be saturated or unsaturated, linear or branched. This $C_8$-$C_{30}$ alkyl chain is most preferably linear. Basic properties of the tensides and emulsifiers are the oriented adsorption at boundary surfaces, as well as the aggregation to micelles and the formation of lyotrophic phases.

When selecting suitable tensides as contemplated herein, it may be preferable to use a mixture of tensides in order to set the properties of the oxidant dye as contemplated herein in an optimal manner.

Anionic tensides suitable for the agents as contemplated herein are all anionic surfactants, suitable for use on the human body, which have an ionic group that renders them water-soluble, for example a sulphate, sulphonate or phosphate group, and a lipophilic alkyl group with approx. 8 to 30 C-atoms, preferably from 8 to 24 C-atoms in the molecule, the exception being linear and branched fatty acids with from 8 to 30 C-atoms and the salts thereof (soaps). Furthermore, the molecule can contain glycol or polyglycol ether groups, ester, ether and amide groups, as well as hydroxyl groups. Examples of suitable anionic tensides, each in the form of the sodium, potassium and ammonium, as well as the mono-, di- and trialkanolammonium salts having from 2 to 4 C-atoms in the alkanol group, polyethoxylated ether carboxylic acids, acylsarcosides, acyltaurides, acylisethionates, sulfosuccinic acid mono- and dialkyl esters and sulfosuccinic acid mono-alkylpolyoxyethylester having from 1 to 6 ethylene oxide groups, linear alkansulfonates, linear alpha-olefinsulfonates, sulfonates of unsaturated fatty acids having up to 6 double bonds, alpha-sulfo fatty acid methylesters of fatty acids, $C_8$-$C_{20}$ alkylsulfates and $C_8$-$C_{20}$ alkylether sulfates having from 1 to 15 oxyethyl groups, mixed surfactant hydroxysulfonates, sulfated hydroxyalkylpolyethylene and/or hydroxyalkylenpropylene glycol ethers, esters of tartaric acid or citric with ethoxylated or propoxylated fat alcohols, where necessary polyethoxylated alkyl- and/or alkenyletherphosphates, sulfated fatty acid alkylenglycol esters, as well as monoglyceridsulfates and monoglyceridethersulfates. Preferred anionic tensides are selected from $C_8$-$C_{20}$ alkylsulfates, $C_8$-$C_{20}$alkylethersulfates and $C_8$-$C_{20}$ ether carboxylic acids, each having from 8 to 20 C-atoms in the alkyl group and from 0 to 12 ethylenoxide groups in the molecule. Sodium laureth(2)sulfate is most preferred.

Zwitterionic tensides are surfactant compounds, which carry a lipophilic alkyl group having approximately from 8 to 30 C-atoms, preferably from 8 to 24 C-atoms and at least one quaternary ammonium group and at least one carboxylate, sulfonate or sulfate group. Particularly suitable zwitterionic tensides are the so-called betaines, such as the n-alkyl-n, n-dimethylammonium glycinates, for example cocoalkyldimethyl ammonium glycinate, n-acylaminopropyl-n, n-dimethyl ammonium glycinates, for example coco-acylaminopropyldimethyl ammonium glycinate (having the INCI trade name of Cocamidopropyl Betaine), and 2-alkyl-3-carboxymethyl-3-hydroxyethyl imidazolines, each having from 8 to 18 carbon atoms in the alkyl or acyl group, as well as coco-acylaminoethylhydroxyethyl carboxymethyl glycinate. A preferred zwitterionic tenside is the coco-acylaminopropyl-dimethyl ammoniumglycinate known under the INCI trade name of Cocamidopropyl Betaine.

Amphoteric tensides are those surfactant compounds containing a $C_8$-$C_{30}$ alkyl or acyl group and at least one free amino group and at least one COOH or —$SO_3H$ group in the molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case from 8 to 30 carbon atoms in the alkyl group. Particularly preferred amphoteric tensides are N-cocosalkylaminopropionate, cocosacylaminoethylaminopropionate and $C_{12}$-$C_{18}$ acylsarcosin.

Preferred anionic or zwitterionic tensides as contemplated herein are selected from $C_8$-$C_{20}$ alkyl sulfates, $C_8$-$C_{20}$ alkylether sulfates and $C_8$-$C_{20}$ ether carboxylic acids, each having from 8 to 20 C-atoms in the alkyl group and from 0 to 12 ethylenoxide groups in the molecule, sodium laureth (2)sulfate being more preferred, also from coco-acylaminopropyl-dimethylammoniumglycinate and from mixtures of said tensides.

Most preferred agents as contemplated herein contain at least one anionic or zwitterionic tenside, selected from $C_8$-$C_{20}$ alkyl sulfates, $C_8$-$C_{20}$-alkyl ether sulfates and $C_8$-$C_{20}$ ether carboxylic acids, each with from 8 to 20 C-atoms in the alkyl group and from 0 to 12 ethylene oxide groups in the molecule, wherein sodium laureth(2)sulphate is particularly preferred, moreover from coco-acylaminopropyl-dimethyl ammonium glycinate, as well as from mixtures of said tensides, in a total quantity of from about 0.1-about 2 wt. %, preferably from about 0.3-about 1.5 wt. %, and most preferably from about 0.5-about 1.2 wt. % relative to the weight of the agent in each case.

A further essential feature of the agent as contemplated herein is a sodium polyacrylate content in a total quantity of from about 0.1-about 1.5 wt. %, preferably from about 0.5-about 1.3 wt. %, most preferably from about 0.8-about 1.1 wt. %, relative to the weight of the agent in each case.

As contemplated herein, sodium polyacrylate preferably comprises polymers with the CAS number 9003-04-7. Sodium polyacrylates preferred as contemplated herein have an average molecular weight Mw in the range from about 1,000,000 to about 20,000,000 Dalton, preferably from about 6,000,000 to about 15,000,000 Dalton. The average molecular weight Mw can, for example, be determined by employing gel permeation chromatography (GPC) with polystyrene as an internal standard according to DIN 55672-3, Version 8/200.

The sodium polyacrylate leads to a further thickening of the agent, the agent taking on the consistency of a creamy gel at the same time.

Agents preferred as contemplated herein contain sodium polyacrylate in a total quantity of from about 0.5-about 1.3 wt. %, preferably from about 0.8-about 1.1 wt. %, relative to the weight of the agent in each case.

In a preferred embodiment, the sodium polyacrylate is contained as a sodium polyacrylate pregelled in a water-oil emulsion. The sodium polyacrylate-containing water-in-oil emulsion preferably contains, in each case relative to its weight, from about 40-about 60 wt. % of sodium polyacrylate, from about 25-about 45 wt. % oil(s) in total, from about 0.5-about 4.9 wt. % tenside(s) in total and from about 0.5-about 4.9 wt. % water.

The oil contained in the sodium polyacrylate-containing water-in-oil emulsion is most preferably selected from natural and synthetic hydrocarbons, most preferably from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from 2-30 carbon atoms with linear or branched saturated or unsaturated fatty acids having from 2-30 carbon atoms, which can be hydroxylated; the adducts of from 1 to 5 propylenoxide units of monovalent or multivalent $C_{8-22}$alkanols; the $C_8$-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkandiols or $C_{3-22}$ alkantriols; the esters of dimers of unsaturated $C_{12}$-$C_{22}$ fat alcohols (dimer fatty acids) having monovalent linear, branched or cyclical $C_2$-$C_{18}$ alkanols or having monovalent linear or branched $C_2$-$C_6$ alkanols; silicone oils, as well as mixtures of the aforementioned substances. The oil most preferred as contemplated herein is mineral oil.

The tenside contained in the sodium polyacrylate-containing water-in-oil emulsion is most preferably from non-ionic tensides. The non-ionic tensides most preferably used are selected from, having from 7-about 80 mol of ethylene oxide per mol, ethoxylated castor oil, ethoxylated $C_8$-$C_{24}$ alkanols having 5-about 30 mol ethylene oxide per mol, ethoxylated $C_8$-$C_{24}$carbonic acid having from 5-about 30 mol of ethylene oxide per mol, having from 4-about 50 mol of ethylene oxide per mol of sorbitan monoesters of linear saturated and unsaturated $C_{12}$-$C_{30}$ carbonic acids, which can be hydroxylated, more particularly those from myristiric acid, palmitic acid, stearic acid of mixtures of said fatty acids, alkylmono and oligoglycosides having from 8 to 22 carbon atoms in the alkyl radical and the ethoxylated analogs thereof, as well as mixtures of the aforementioned substances.

The ethoxylated $C_8$-$C_{24}$ alkanols have the formula $R^1O(CH_2CH_2O)_nH$, wherein $R^1$ denotes a linear or branched alkyl and/or alkenyl radical having 8-24 carbon atoms and n, the average number of ethylene oxide units per molecule, for integers from 5-about 30, preferably 6-about 20, more preferably from 6 to 12 mol ethylene oxide to 1 mol alkanol, which is preferably selected from capryl alcohol, 2-ethylhexyl alcohol, caprin alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, as well as the technical mixtures thereof. Adducts from 10-about 100 mol ethylene oxide on technical fat alcohols having from 12-18 carbon atoms, such as for example coco, palm, palm kernel or sebum fat alcohols are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20 and Coceth-30 are more preferred; Trideceth-6 and Isotrideceth-6, as well as the mixtures thereof, are most preferred.

The ethoxylated $C_8$-$C_{30}$ carbonic acids have the formula $R^1O(CH_2CH_2O)_nH$, wherein $R^1O$ denotes a linear or branched, saturated or unsaturated acyl radical having 8-30 carbon atoms and n, the average number of ethylene oxide units per molecule, for integers from 5-about 30, preferably from 6-about 20, more preferably from 6 to 12 mol ethylene oxide to 1 mol $C_8$-$C_{30}$ carbonic acid, which is preferably selected from capryl alcohol, 2-ethylhexyl alcohol, caprin alcohol, lauric acid, isotridecaric acid, myristiric acid, cetyl acid, palmitoleic acid, stearic acid, isostearic acid, oleic acid, elaidic acid, petroselic acid, arachine acid, gadoleic acid, behen acid, eruca acid and brassidic acid, as well as the technical mixtures thereof. Adducts from 5-about 30, preferably from 6-about 20, more preferably from 6 to 12 mol of ethylene oxide on technical fatty acids having from 12-18 carbon atoms, such as coco, palm, palm kernel or sebum fat alcohols are also suitable.

Agents most preferred as contemplated herein are exemplified in that they contain at least one sodium polyacrylate having an average molecular weight Mw in the range from about 1,000,000 to about 20,000,000 Dalton, preferably from about 6,000,000 to about 15,000,000 Dalton, in a total quantity of from about 0.1-about 1.5 wt. %, preferably from about 0.5-about 1.3 wt. %, more preferably from about 0.8-about 1.1 wt. %, in each case relative to the total weight of the agent, wherein the sodium polyacrylate is contained pregelled in a water-in-oil emulsion, wherein said water-in-oil emulsion, in each case relative to its weight, contains from about 40-about 60 wt. % sodium polyacrylate, from about 25-about 45 wt. % oil(s) in total, preferably mineral oil, from about 0.5-about 4.9 wt. % tenside(s) in total, preferably from about 0.5-about 4.9 wt. % niotenside(s), and from about 0.5-about 4.9 wt. % water.

Agents as contemplated herein, which contain sodium polyacrylate, have a viscosity in the range of from about 10,000-about 75,000 mPas, preferably from about 12,000-about 60,000 mPas, more preferably from about 13,000-about 50,000 mPas, most preferably from about 15,000-about 25,000 mPas, in each case measured at 20° C. by employing a Brookfield rotational viscometer at a rotational frequency of 4 rpm with Spindle 5.

Agents preferred as contemplated herein are exemplified by a content of at least one cross-linked copolymer, constructed from acrylic acid and non-ethoxylated esters of acrylic acid with linear C10-C30 mono-alcohols as monomers, wherein the cross-linked copolymer is contained in a total quantity of from about 0.05-about 2 wt. %, preferably from about 0.1-about 1.5 wt. %, more preferably from about 0.3-about 1 wt. %, most preferably from about 0.5-about 0.8 wt. %, in each case relative to the weight of the agent. The at least one cross-linked copolymer from acrylic acid and non-ethoxylated esters of acrylic acid having linear C10-C30 mono-alcohols is preferably selected from copolymers having the INCI trade name of Acrylates/C10-30 Alkyl Acrylate Crosspolymer. Sucrose allyl ether or pentaerythrityl allyl ether is preferably contained as the cross-linking agent.

Cross-linked copolymers from acrylic acid and non-ethoxylated esters of acrylic acid having linear C10-C30 mono-alcohols, which are most preferred as contemplated herein, can be obtained by polymerizing a monomer mixture which—in each case relative to its weight—contains from about 80 to about 99 wt. %, preferably from about 90 to about 98 wt. %, acrylic acid, at least one non-ethoxylated ester of acrylic acid having linear C10-C30 mono-alcohols in a total quantity of from about 0.9-about 19.9 wt. %, preferably from about 2-about 10 wt. %, as well as a cross-linking agent in a total quantity of from about 0.1-about 4 wt. %.

Other cross-linked copolymers from acrylic acid and non-ethoxylated esters having linear C10-C30 mono-alcohols, which are most preferred as contemplated herein, are exemplified in that their 0.5 wt. % dispersion in water at 25° C. and a pH value in the range of from about 5.8-about 6.3 has a viscosity in the range of from about 45,000 to about 65,000 mPas, measured by employing a Brookfield RVF or a Brookfield RVT viscometer at a rotational frequency of 20 rpm with Spindle #7.

The content of the at least one cross-linked copolymer, constructed from acrylic acid and non-ethoxylated esters with acrylic acid having linear C10-C30 mono-alcohols as monomers, is preferably selected such that the viscosity of the agent as contemplated herein is within the range of from about 10,000-about 75,000 mPas, preferably from about 12,000-about 60,000 mPas, more preferably from about 13,000-about 50,000 mPas, most preferably from about 15,000-about 25,000 mPas, in each case measured at 20° C. by employing a Brookfield rotational viscometer at a rotational frequency of 4 rpm with Spindle 5.

The agents as contemplated herein and used as contemplated herein contain, in each case relative to their weight, at least one linear saturated alcohol having two or three hydroxy groups and from 2 to 8 carbon atoms in the alkyl group in a total quantity of from about 0-about 3 wt. %, preferably from about 0.1-about 2.2 wt. %. Particularly preferred linear saturated alkanols having two or three hydroxy groups and from 2 to 8 carbon atoms in the alkyl group are selected from 1,2-propandiol and glycerine, as well as mixtures thereof. Most preferred are from about 0-about 3 wt. %, preferably from about 0.1-about 2.2 wt. % 1,2-propandiol, in each case relative to the weight of the agent. At least one linear saturated alkanol having two or three hydroxy groups and from 2 to 8 carbon atoms in the alkyl group, including 1,2-propandiol is also preferably contained, in a total quantity of from about 0-about 3 wt. %, preferably from about 0.1-about 2.2 wt. %, in each case relative to the weight of the agent.

The agents as contemplated herein and used as contemplated herein do not contain any saturated or unsaturated non-alkoxylated alkanols having a hydroxy group and from 1 to about 50 carbon atoms in the alk(en)yl group; more particularly, the agents as contemplated herein contain no ethanol, no isopropanol, no linear fatty alcohols such as cetyl- or stearyl alcohol, and no branched alkanols, such as 2-octyldodecanol.

Moreover, the agents as contemplated herein contain no saturated or unsaturated alkan carbonic acids having from 1 to about 50 carbon atoms, more particularly no oleic acids and no stearic acids or the salts thereof.

Agents preferred as contemplated herein and preferably used as contemplated herein are exemplified in that they contain, relative to their weight, polyethylenglycol(s) having an average molecular weight of from about 100 to about 100,000 g·mol$^{-1}$ in a total quantity of from about 0-about 0.2 wt. %, preferably from about 0-about 0.1 wt. %. As contemplated herein, polyethylene glycols are compounds of the formula $HO(CH_2CH_2O)_nH$, wherein the index n denotes the degree of polymerization and is an integer from 3-about 2300.

It has emerged that saturated and unsaturated non-alkoxylated alkanols having a hydroxy group and from 1 to about 50 carbon atoms in the alk(en)yl group, more particularly ethanol and isopropanol, also linear saturated alkanols with two or three hydroxy groups and from 2 to 8 carbon atoms in the alkyl group and polyethylene glycols having an average molecular weight from about 100 to about 100,000 g·mol$^{-1}$ have a negative impact on the quality of the gel consistency, and therefore the total content thereof, as described above, should be limited and as low as possible.

Moreover, agents preferred as contemplated herein and preferably used as contemplated herein preferably contain fatty substances having a melting point of about 30° C. and above at 1013 mbar and a water-solubility of about 0.005 wt. % and below in a total quantity of from about 0-about 0.1 wt. %, preferably 0 wt. %, relative to the weight of the agent. Said fatty substances include waxes, hardened oils and fats, as well as esters from fatty acids and fat alcohols having a melting point of about 30° C. and over at 1013 mbar.

Agents preferred as contemplated herein and preferably used as contemplated herein contain, in each case relative to their weight, at least one oil in a total quantity of from about 0.1 to about 2 wt. %, preferably from about 0.2-about 1.5 wt. %, most preferably from about 0.5-about 1 wt. %.

A further essential feature of the agent as contemplated herein is the content of at least one oxidation dye precursor.

On the basis of their reaction behavior, oxidative dye precursors can be divided into two categories, so-called developer components and coupler components.

During the oxidative dyeing process, coupler components do not achieve any significant coloration by themselves. They always require the presence of developer components. Developer components can combine together to form the actual dye.

The developer and coupler components are normally used in a free form. In the case of substances with amino groups, however, use of the salt form thereof, more particularly in the form of hydrochlorides and hydrobromides or sulfates, may be preferred. Oxidation dye precursors include oxidation dye precursors of the developer and coupler types. Particularly suitable oxidation dye precursors of the developer type are selected from at least one compound from the group of p-phenylenediamine, p-toluylenediamine, 2-(2-hydroxyethyl)-p-phenylenediamine, 2-(1,2-dihydroxyethyl)-p-phenylenediamine, N,N-bis(2-hydroxyethyl)-p-phenylenediamine, 2-methoxymethyl-p-phenylenediamine, N-(4-amino-3-methylphenyl)-N-[3-(1H-imidazol-1-yl) propyl] amine, N,N'-bis(2-hydroxyethyl)-N,N'-bis-(4-aminophenyl)-1,3-diamino-propane-2-ol, bis-(2-hydroxy-5-aminophenyl) methane, 1,3-bis(2,5-diaminophenoxy) propan-2-ol, N, N'-bis(4-aminophenyl)-1,4-diazacycloheptane, 1,10-bis (2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl) phenol, 4-amino-2-(diethylaminomethyl) phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H, 5H-pyrazolo [1,2-a] pyrazol-1-one and the physiologically tolerated salts thereof. Most preferred developer components are selected from p-toluylendiamine, 2-(2-hydroxyethyl)-p-phenylendiamine, N,N-bis-(2-hydroxyethyl)-p-phenylendiamine, 2-methoxymethyl-p-phenylendiamine and/or 4,5-diamino-1-(2-hydroxyethyl)-pyrazol and the physiologically tolerated salts and mixtures thereof.

Particularly suitable oxidation dye precursors of the coupler type are selected from the group of 3-aminophenol, 5-amino-2-methylphenol, 3-amino-2-chlor-6-methylphenol, 2-hydroxy-4-aminophenoxyethanol, 5-amino-4-chlor-2-methylphenol, 5-(2-hydroxyethyl)-amino-2-methylphenol, 2,4-dichlor-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzol (2-amino-4-[(2-hydroxyethyl)amino]-anisol), 1,3-bis(2,4-diaminophenyl)propane, 2,6-bis(2'-hydroxyethylamino)-1-methylbenzol, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis(2-hydroxyethyl)aminobenzol, resorcin, 2-methylresorcin, 4-chlorresorcin, 1,2,4-trihydroxybenzol, 2-amino-3-hydroxypyridin, 3-amino-2-methylamino-6-methoxypyridin, 2,6-dihydroxy-3,4-dimethylpyridin, 3,5-diamino-2,6-dimethoxypyridin, 1-phenyl-3-methylpyrazol-5-on, 1-naphthol, 1,5-dihydroxynaphthalin, 2,7-dihydroxynaphthalin, 1,7-dihydroxynaphthalin, 1,8-dihydroxynaphthalin, 4-hydroxyindol, 6-hydroxyindol, 7-hydroxyindol, 4-hydroxyindolin, 6-hydroxyindolin, 7-hydroxyindolin or mixtures of said compounds or the physiologically compatible salts thereof. Most preferred coupler components are selected from 3-aminophenol, 5-amino-2-methylphenol, 3-amino-2-chlor-6-methylphenol, 2-hydroxy-4-aminophenoxyethanol, 2-(2, 4-diaminophenoxy)ethanol, 1-methoxy-2-amino-4-(2-hydroxyethylamino)benzol (2-Amino-4-[(2-hydroxyethyl) amino]-anisol), resorcin, 2-methylresorcin, 4-chlorresorcin, 2-amino-3-hydroxypyridin, as well as the physiologically compatible salts and mixtures thereof.

In a preferred embodiment, the dyes as contemplated herein contain one or more oxidation dye precursors in a total quantity from about 0.001 to about 5.0 wt. %, preferably from about 0.01 to about 4.0 wt. %, more preferably from about 0.2 to about 3.5 wt. %, even more preferably from about 0.3 to about 2.5 wt. % and most preferably from about 0.7 to about 1.8 wt. %, relative to the weight of the dye as contemplated herein and/or the weight of the composition used as contemplated herein (M1).

In a preferred embodiment, the dyes as contemplated herein contain one or more oxidation dye precursors, selected from at least one developer component and optionally at least one coupler component, in a total quantity from about 0.001 to about 5.0 wt. %, preferably from about 0.01 to about 4.0 wt. %, more preferably from about 0.2 to about 3.5 wt. %, even more preferably from about 0.3 to about 2.5 wt. % and most preferably from about 0.7 to about 1.8 wt. %, relative to the weight of the dye as contemplated herein and/or the weight of the composition used as contemplated herein (M1).

In a more preferred embodiment of the present disclosure, the agent as contemplated herein contains at least one partially-oxidizing dye.

In oxidative hair dyes, partially-oxidizing dyes often serve to tint unwanted red undertones, which can be produced by the melanin decomposition products, or to tint certain blond tones.

In order to obtain a balanced and subtle tint formation, the present disclosure may specify that the cosmetic agents with ODP additionally contain at least one partially-oxidizing dye.

Partially-oxidizing dyes are dyes that coat the substrate itself and do not require an oxidative process to create the color. Partially-oxidizing dyes are usually nitro-phenylendiamines, nitroaminophenols, azo dyes, anthraquinones or indophenols.

Partially-oxidizing dyes can be sub-divided into anionic, cationic and non-ionic partially-oxidizing dyes.

Preferred anionic partially-oxidizing dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and tetrabromphenol blue.

Preferred cationic partially-oxidizing dyes are cationic triphenylmethane dyes, such as Basic Blue 7, Basic Blue 26, Basic Violet 2 and Basic Violet 14, as well as aromatic systems, which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methyl-benzol, 1-amino-4-(2-hydroxyethyl)amino-5-chlor-2-nitrobenzol, 4-amino-3-nitrophenol, 1-(2'-Ureidoethyl) amino-4-nitrobenzol, 2-[(4-amino-2-nitrophenyl)amino] benzoic acid, 6-nitro-1,2,3,4-tetrahydrochinoxalin, 2-hydroxy-1,4-naphthochinon, picramic acid and the salts thereof, 2-amino-6-chloro-4-nitrophenol, 4-ethylamino-3-nitrobenzoic acid and 2-chlor-6-ethylamino-4-nitrophenol.

Moreover, partially-oxidizing dyes that occur in nature, such as Henna red, Henna neutral, Henna black, chamomile blossoms sandalwood, black tea, walnut, Cascara bark, sage, logwood, madder root, catechu, ceder and alkanna root, can also be used.

The cosmetic agent according preferably contains at least one partially-oxidizing agent in a total quantity of from about 0.001 to about 10 wt. %, preferably from about 0.01 to about 8 wt. %, more preferably from about 0.1 to about 5 wt. %, most preferably from about 0.5 to about 2 wt. %, relative to the total weight of the cosmetic agent and/or of the composition used as contemplated herein (M1).

Therefore, a further subject of the present disclosure is a kit-of-parts, comprising—packaged separately from one another:

a) at least one container (C1), containing an agent for oxidative hair dyeing containing the following, in each case relative to its weight:
   from about 70 to about 95 wt. % water,
   at least one oxidation dye precursor,
   at least one alkalizing agent,
   at least one tenside, selected from anionic, zwitterionic and amphoteric tensides, as well as mixtures thereof, in a total quantity of from about 0.1-about 2 wt. %,
   Sodium polyacrylate in a total quantity of from about 0.1-about 1.5 wt. %, preferably from about 0.5-about 1.3 wt. %, more preferably from about 0.8-about 11 wt. %, preferably with an average molecular weight Mw in the range from about 1,000,000 to about 20,000,000 Dalton, preferably from about 6,000,000 to about 15,000,000 Dalton,
   at least one linear, saturated alkanol with two or three hydroxy groups and from 2 to 8 carbon atoms in the alkyl group in a total quantity of from about 0-about 3 wt. %, wherein
   no saturated or unsaturated non-alkoxylated alkanols with a hydroxy group and from 1 to about 50 carbon atoms in the alk(en)yl group and
   no saturated or unsaturated alkanecarboxylic acids with 1 to 50 carbon atoms, and
   no oxidants
are included in the agent, and b) at least one container (C2), containing an oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and which has a pH value in the range from about 2.0 to about 6.5, preferably from about 2.5-about 5.5, more preferably from about 2.8 to about 5.0, in each case measured at 20° C., wherein each of the wt. % values are relative to the weight of the oxidant preparation (M2).

A further subject matter of the present disclosure is a method for oxidative hair dyeing comprising the following method steps:

i) Providing a cosmetic agent (M1) for the oxidative hair dyeing of keratinic fibers, containing
   from about 70 to about 95 wt. % water,
   at least one oxidation dye precursor,
   at least one alkalizing agent,
   at least one tenside, selected from anionic, zwitterionic and amphoteric tensides, as well as mixtures thereof, in a total quantity of from about 0.1-about 2 wt. %, Sodium polyacrylate in a total quantity of from about 0.1-about 1.5 wt. %, preferably from about 0.5-about 1.3 wt. %, more preferably from about 0.8-about 11 wt. %, preferably with an average molecular weight Mw in the range from about 1,000,000 to about 20,000,000 Dalton, preferably from about 6,000,000 to about 15,000,000 Dalton, at least one linear, saturated alkanol with two or three hydroxy groups and from about 2 to about 8 carbon atoms in the alkyl group in a total quantity of from about 0-about 3 wt. %, wherein no saturated or unsaturated non-alkoxylated alkanols with a hydroxy group and from 1 to about 50 carbon atoms in the alk(en)yl group and no saturated or unsaturated alkanecarboxylic acids with from 1 to about 50 carbon atoms, and no oxidants are included in the agent, ii) Providing at least one oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and which has a pH value in the range from about 2.0 to about 6.5, preferably from v2.5-about 5.5, more preferably from about 2.8 to about 5.0, in each case measured at 20° C., wherein each of the wt. % values are relative to the weight of the oxidant preparation (M2), wherein at least one cation tenside is optionally contained, iii) Mixing the cosmetic agent (M1) with the oxidant preparation (M2), preferably in a weight ratio (M1):(M2) in the range from about 1:0.8 to about 1:2.5, preferably from about 1:1 to about 1:2, immediately afterwards iv) Applying the mixture obtained in Step iii) onto the hair and leaving said mixture for a period of from about 1 to about 60 minutes, preferably from about 20 to about 45 minutes at room temperature and/or at from about 30-about 60° C., preferably at from about 32-about 50° C. on the hair, v) Rinsing the hair with water and/or a cleansing composition, and vi) where necessary, applying a post-treatment agent onto the hair and, where necessary, rinsing out, then drying.

For oxidative hair dyeing, immediately before the application on the hair, the one or more oxidation dye precursors and, where applicable, one or more partially-oxidizing dyes, are usually mixed with a hydrous oxidant-containing composition (M2) to produce the ready-to-use dye and then applied to the hair. In most cases, the agent as contemplated herein (M1) and the oxidant-containing composition (M2) are matched with one another such that, at a mixing ratio of 1 to 1, relative to the parts by weight, the ready-to-use application mixture has an initial concentration of hydrogen peroxide of from about 0.5-about 12 wt. %, preferably from about 2-about 10 wt. %, more preferably from about 3-about 6 wt. % of hydrogen peroxide (calculated as 100% $H_2O_2$), in each case relative to the weight of the application mixture. However, it is equally possible for the agent as contemplated herein (M1) and the oxidant-containing composition (M2) to be matched to one another such that the concentrations required in the ready-to-use oxidant dye (application mixture) is achieved through mixture ratios other than 1:1, for example through a weight-based mixture ratio of 1:2 or 1:3 or even 2:3.

Weight-based mixture ratios preferred as contemplated herein (M1):(M2) are within the range from about 1:0.8 to about 1:2.5, more preferably within the range of from about 1:1 to about 1:2.

As contemplated herein, the expression "room temperature" describes the temperature inside the room in which a person would usually use a hair dye, i.e. usually a bathroom or a hairdressing salon, in which a temperature within the range of from about 10-about 29° C. prevails.

The leaving of the hair dyeing application mixture in method step iv) in the hair dyeing method as contemplated herein or preferred as contemplated herein can also occur at a minimum of about 30° C., preferably at from about 30-about 60° C., more preferably at from about 32-about 50° C., if the hair is heated by employing a heating hood or a heat radiator, for example.

The oxidant preparation (M2) used in the dye kit as contemplated herein and preferred as contemplated herein, as well as in the dyeing method as contemplated herein and preferred as contemplated herein contains, in each case relative to the weight thereof, from about 40-about 96 wt. %, preferably from about 70-about 93 wt. %, most preferably from about 80-about 90 wt. % of water.

The oxidant preparation (M2) used in the dye kit as contemplated herein and preferred as contemplated herein, as well as in the dyeing method as contemplated herein and preferred as contemplated herein contains, in each case relative to the weight thereof, from about 0.5 to about 23 wt. %, preferably from about 2.5 to about 21 wt. %, more preferably from about 4 to about 20 wt. %, even more preferably from about 5 to about 18 wt. and most preferably from about 6 to about 12 wt. % of hydrogen peroxide.

To stabilize the hydrogen peroxide, the oxidant preparation (M2) has a pH value in the range from about 2.0 to about 6.5, preferably from about 2.5-about 5.5, most preferably from about 2.8 to about 5.0, in each case measured at 20° C.

The relatively low viscosity of the agent preferred as contemplated herein (M1) in the range of from about 10,000-about 75,000 mPas, preferably from about 12,000-about 60,000 mPas, more preferably from about 13,000-about 50,000 mPas, most preferably from about 15,000-about 25,000 mPas, in each case measured at 20° C. by employing a Brookfield rotational viscometer at a rotational frequency 4 rpm with Spindle 5, is ideally suited to handle this agent per se (production, placing in plastic bottles, dispensing to produce the mixture with the oxidant preparation).

Cation Tenside in the Oxidant Preparation (M2)

The oxidant preparation (M2) usually has a low viscosity in the range of from about 10-about 6000 mPas, preferably from about 200-about 5000 mPas, more preferably from about 1000-about 4500 mPas, in each case measured at 20° C. For application on the hair, however, the application mixture ought to have a substantially higher viscosity so that it remains on the hair for the entire exposure time (in the range of from about 5-about 60 minutes, preferably from about 30-about 45 minutes) without dripping. A distinction is drawn here as to whether the application mixture is produced by shaking the two compositions (M1) and (M2) in an application bottle, from which the application mixture is applied to the hair immediately after mixing by employing an application nozzle in the form of a bottle attachment (bottle application), or whether the application mixture is produced by stirring the two compositions (M1) and (M2) in a bowl, from which the application is mixture is applied to the hair immediately after mixing by employing a brush (brush application). The bottle application is particularly suitable for dyes that are sold in retail outlets trade with an application recommendation by the consumer itself. The brush application is particularly suitable for dyes that are produced in the hairdressing salon and applied to the consumer's hair by the hairdresser.

It has unexpectedly emerged that an application mixture having a viscosity particularly suitable for brush application is obtained if the agent as contemplated herein or preferred as contemplated herein (M1) is mixed with an oxidant preparation (M2) containing at least one cation tenside. During the mixing process, the interaction between the at least one sodium polyacrylate and the at least one cation tenside leads to the desired viscosity increase. The pasty consistency of the application mixture thus obtained leads to optimum application properties, more particularly for the brush application. The application mixtures thus achieved, preferably with weight-based mixture ratios (M1):(M2) in the range of from about 1:0.8 to about 1:2.5, more preferably in the range of from about 1:1 to about 1:2, preferably have a viscosity in the range of from about 10000-about 100000 mPas, more preferably from about 12000-about 80000 mPas, most preferably from about 15000-about 40000 mPas, in each case measured at 20° C. (Brookfield viscometer, at a rotational frequency of 4 rpm with Spindle No. 5).

In a more preferred embodiment of the present disclosure, the oxidant preparation used as contemplated herein (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2).

Cationic tensides are tensides, i.e. surfactant compounds, each having one or more positive charges. Cationic tensides contain exclusively positive charges. Usually, said tensides are constructed from a hyrdophobic part and a hydrophilic head group, wherein the hydrophobic part normally includes a hydrocarbon structure (e.g. including one or two linear or branched alkyl chains), and the positive charge(s) are localized in the hydrophilic head group. Cationic tensides adsorb at boundary surfaces and aggregate in hydrous solutions above the critical micelle formation concentration to form positively charged micelles.

As contemplated herein, preferred cationic tensides are of the type of quaternary ammonium compounds, eterquats and alkyl amidoamines. Preferred quaternary ammonium compounds are ammonium halogenides, such as alkyltrimethylammoniumchloride, dialkyldimethylammoniumchloride, trialkylmethylammoniumchloride, as well as the imidazolium compounds known under the INCI trade names of Quatemium-27 and Quatemium-83. Other preferred quaternery ammonium compounds are tetra alkyl ammonium salts, such as that known under the INCI trade name of Quaternium-52, a poly(oxy-1,2-ethanediyl), ((octadecylnitrilio)tri-2,1-ethanediyl)tris(hydroxy)-phosphate (1:1)-salt, which has the general structural formula (III), wherein x+y+z=10 are

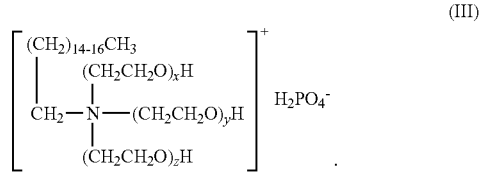

The long alkyl chains of the aforementioned tensides preferably have from 10 to about 22, more preferably from 12 to 18 carbon atoms. Particularly preferred are behenyl trimethyl ammonium chloride, stearyl trimethyl ammonium chloride and cetyl trimethyl ammonium chloride, wherein stearyl trimethyl ammonium chloride is most preferred. Other suitable cationic tensides as contemplated herein are quaternary protein hydrolysates. Alkylamidoamines are usually produced through the amidation of natural or synthetic fatty acids and fatty acid molecules with dialkylaminoamines. As contemplated herein, Tegoamid® S 18 (stearamidopropyldimethylamin) is a suitable compound from this substance group. Esterquats are substances containing both at least one ester function and at least quaternary ammonium group as the structural element. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines. Such products are sold under the trade names of Stepantex, Dehyquart and Armocare.

With respect to optimum application properties and optimum dye results, C10-C22 alkyl trimethyl ammonium chloride has proved to be particularly suitable. Particularly preferred oxidant preparations used as contemplated herein (M2) are therefore exemplified in that they contain at least one cation tenside in a total quantity from about 0.1-about 1.5 wt. %, most preferred from about 0.3-about 0.9 wt. %, in each case relative to the weight of the oxidant preparation (M2), wherein preferably at least one tenside, selected from C10-C22 alkyl trimethyl ammonium chlorides, most preferably selected from behenyl trimethyl ammonium chloride, stearyl trimethyl ammonium chloride and cetyl trimethyl ammonium chloride, as well as mixtures of said tensides, is contained. Oxidant preparations most preferred as contemplated herein (M2) contain stearyltrimethylammoniumchloride in a total quantity from about 0.05-about 3 wt. %, preferably from about 0.1-about 1.5 wt. %, more preferably from about 0.3-about 0.9 wt. %, in each case relative to the weight of the oxidant preparation (M2).

A further kit-of-parts preferred as contemplated herein is exemplified in that the oxidant preparation (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

It has emerged that the thickening aided by the interaction between the copolymer in the agent as contemplated herein and the cation tenside in the oxidant preparation (M2) is adequate, and due to the presence of a polymer with a polymerization degree of at least about 200 or a polymer with a molecular weight of about 10,000 Dalton or higher, is unable to further increase and/or even be adversely affected in terms of its application properties.

A further kit-of-parts preferred as contemplated herein is exemplified in that the oxidant preparation (M2) contains at least one cation tenside, which is preferably selected from stearyltrimethyl ammonium chloride, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

A method for oxidative hair dyeing as contemplated herein is exemplified in that the oxidant preparation (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

A further method for oxidative hair dyeing as contemplated herein is exemplified in that the oxidant preparation (M2) contains at least one cation tenside, which is preferably selected from stearyltrimethyl ammonium chloride, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), but contains no polymer with a polymerization degree of at least about 200 and no polymer with a molecular weight of about 10,000 Dalton or higher.

It has unexpectedly emerged that an application mixture having a viscosity particularly suitable for bottle application is obtained if the agent as contemplated herein or preferred as contemplated herein (M1) is mixed with an oxidant preparation (M2) containing at least one copolymer, selected from cross-linked acrylic acid/acrylic acid-C1-C6-alkyl ester copolymers and cross-linked methacrylic acid/acrylic acid-C1-C6-alkyl ester copolymers, preferably in a total quantity from about 0.1-about 7 wt. %, more preferably from about 0.5-about 6 wt. %, most preferably from about 1-about 4.5 wt. %, in each case relative to the weight of the oxidant preparation (M2). The mixing of the agent as contemplated herein or preferred as contemplated herein with such an oxidation preparation (M2) leads to the desired viscosity increase. The medium-viscosity consistency of the application mixture thus obtained leads to optimum application properties, more particularly for the bottle application. The application mixtures thus achieved, preferably with weight-based mixture ratios (M1):(M2) in the range of from about 1:0.8 to about 1:2.5, more preferably in the range of from about 1:1 to about 1:2, preferably have a viscosity in the range of from about 2000-about 50,000 mPas, more preferably from about 5000-about 40,000 mPas, even more preferably from about 8,000-about 30,000 mPas, most preferably from about 11,000-about 24,000 mPas, in each case measured at 20° C. (Brookfield viscometer, at a rotational frequency of 4 rpm with Spindle No. 5).

A further kit-of-parts preferred as contemplated herein is exemplified in that the oxidant preparation (M2) contains at least one copolymer, selected from cross-linked acrylic acid/acrylic acid —C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cation tenside.

A further method for oxidative hair dyeing as contemplated herein is exemplified in that the oxidant preparation (M2) contains at least one copolymer, selected from cross-linked acrylic acid/acrylic acid —C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cation tenside.

Preferred cross-linked copolymers of this type are selected from—in each case cross-linked—methacrylic acid/methylacrylate-, methacrylic acid/ethylacrylate-, methacrylic acid/propylacrylate-, methacrylic acid/butylacrylate-, methacrylic acid/pentylacrylate-, methacrylic acid/hexylacrylate-, acrylic acid/methylacrylate-, acrylic acid/ethylacrylate-, acrylic acid/propylacrylate-, acrylic acid/butylacrylate-, acrylic acid/pentylacrylate- and acrylic acid/hexylacrylate copolymers and the mixtures thereof.

A further kit-of-parts preferred as contemplated herein is exemplified in that the oxidant preparation (M2) contains at least one cross-linked copolymer, selected from—in each case cross-linked—methacrylic acid/methylacrylate-, methacrylic acid/ethylacrylate-, methacrylic acid/propylacrylate-, methacry acid/butyl acrylate-, methacrylic acid/pentylacrylate-, methacrylic acid/hexylacrylate-, acrylic acid/methyl acrylate-, acrylic acid/ethyl acrylate-, acrylic acid/propylacrylate-, acrylic acid/butylacrylate, acrylic acid/pentyl acrylate- and acrylic acid/hexylacrylate-copolymers and mixtures thereof, in a total quantity from about 0.1-about 7 wt. %, preferably from about 0.5-about 6 wt. %, most preferably from about 1-about 4.5 wt. %, in each case relative to the weight of the oxidant preparation (M2), and no cation tenside.

A further method preferred as contemplated herein is exemplified in that the oxidant preparation (M2) contains at least one cross-linked copolymer, selected from—in each case cross-linked—methacrylic acid/methylacrylate-, methacrylic acid/ethylacrylate-, methacrylic acid/propylacrylate-, methacry acid/butyl acrylate-, methacrylic acid/pentylacrylate-, methacrylic acid/hexylacrylate-, acrylic acid/methyl acrylate-, acrylic acid/ethyl acrylate-, acrylic acid/propylacrylate-, acrylic acid/butylacrylate, acrylic acid/pentyl acrylate- and acrylic acid/hexylacrylate-copolymers and mixtures thereof, in a total quantity from about 0.1-about 7 wt. %, preferably from about 0.5-about 6 wt. %, most preferably from about 1-about 4.5 wt. %, in each case relative to the weight of the oxidant preparation (M2), and no cation tenside.

Moreover, the oxidant preparations as contemplated herein and preferred as contemplated herein (M2) can contain stabilizers, more particularly complexing agents, and pH buffer substances.

In a more preferred embodiment of the present disclosure, the oxidant preparation used as contemplated herein (M2) contains at least one oil in a total quantity of from about 0.2-about 50 wt. %, preferably from about 2-about 40 wt. %, more preferably from about 8-about 30 wt. %, most preferably from about 15-about 25 wt. %, in each case relative to the weight of the oxidant preparation (M2).

In a most preferred embodiment of the present disclosure, the oxidant preparation used as contemplated herein (M2) contains at least one oil in a total quantity of from about 0.2-about 50 wt. %, preferably from about 2-about 40 wt. %, more preferably from about 8-about 30 wt. %, most preferably from about 15-about 25 wt. %, in each case relative to the weight of the oxidant preparation (M2).

The at least one oil contained in the oxidant preparation (M2) in a total quantity of from about 0.2-about 50 wt. %, relative to the weight of the preparation (M2), is preferably selected from natural and synthetic hydrocarbons, most preferably from mineral oil, paraffin oils, $C_{18}$-$C_{30}$ isoparaffins, particularly isoeicosane, polyisobutenes and polydecenes, $C_8$-$C_{16}$ isoparaffins, as well as 1,3-di-(2-ethylhexyl)-cyclohexane; the benzoic acid esters of linear or branched $C_{8-22}$ alkanols; triglycerides of linear or branched, saturated or unsaturated, where necessary hydroxylated $C_{8-30}$ fatty acids, particularly natural oils; the dicarboxylic acid esters of linear or branched $C_2$-$C_{10}$ alkanols; the esters of linear or branched saturated or unsaturated fat alcohols having from 2-about 30 carbon atoms with linear or branched saturated or unsaturated fatty acids having from 2-about 30 carbon atoms, which can be hydroxylated; the adducts of from 1 to 5 propylenoxide units of monovalent or multivalent $C_{8-22}$alkanols; the $C_8$-$C_{22}$ fatty alcohol esters of monovalent or multivalent $C_2$-$C_7$hydroxycarboxylic acids; the symmetrical, asymmetrical or cyclical esters of carbonic acids having $C_{3-22}$ alkanols, $C_{3-22}$ alkandiols or $C_{3-22}$ alkantriols; the esters of dimers of unsaturated $C_{12}$-$C_{22}$ fat alcohols (dimer fatty acids) having monovlaent linear, branched or cyclical $C_2$-$C_{18}$ alkanols or having monovalent linear or branched $C_2$-$C_6$ alkanols; silicone oils, as well as mixtures of the aforementioned substances. In this context, oils particularly preferred as contemplated herein are selected from paraffin oils and the esters of linear or branched saturated or unsaturated fat alcohols having from 2-about 30 carbon atoms with linear or branched fatty acids having from 2-about 30 carbon atoms, which can be hydroxylated, as well as mixtures thereof, most preferred oils are selected from paraffin oil, isopropylpalmitate and isopropylmyristate, as well as mixtures thereof.

In a more preferred embodiment of the present disclosure, the oxidant preparation used as contemplated herein (M2) contains at least one tenside, selected from anion tensides and niotensides, as well as mixtures thereof, in a total quantity of from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachylalcohol), as well as mixtures thereof, in a total quantity from about 1-about 5 wt. %, preferably from about 1.5-about 4 wt. %, wherein the quantity values are relative to the weight of the oxidant preparation (M2), and wherein the preparation (M2) contains no cation tensides, no oils, no polymers with a polymerization degree of at least about 200 and no polymers with a molecular weight of about 10,000 Dalton or higher.

A more preferred kit-of-parts as contemplated herein and a more preferred hair dyeing method as contemplated herein are each exemplified in that the oxidation preparation (M2) contains at least one tenside, selected from anion tensides and niotensides, as well as mixtures thereof, in a total quantity of from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, each relative to the weight of the oxidant preparation (M2).

A more preferred kit-of-parts as contemplated herein and a more preferred hair dyeing method as contemplated herein are each exemplified in that the oxidation preparation (M2) contains at least one tenside, selected from anion tensides and niotensides, as well as mixtures thereof, in a total quantity of from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, each relative to the weight of the oxidant preparation (M2), although no polymers having a polymerization degree of at least about 200 and no polymer having a molecular weight of about 10,000 Dalton or higher.

It has emerged that the thickening aided by the interaction between the copolymer in the agent as contemplated herein and the aforementioned tenside/1-alkanol mixture in the oxidant preparation (M2) is adequate, and due to the presence of a polymer with a polymerization degree of at least about 200 or a polymer with a molecular weight of about 10000 Dalton or higher, is unable to further increase and/or even be adversely affected in terms of its application properties.

A more preferred kit-of-parts as contemplated herein and a more preferred hair dyeing method as contemplated herein are each exemplified in that the oxidation preparation (M2) contains at least one tenside, selected from anion tensides and niotensides, as well as mixtures thereof, in a total quantity of from about 0.05-about 2 wt. %, preferably from about 0.3-about 1.5 wt. %, at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, and at least one oil in a total quantity of from about 0.2-about 50 wt. %, preferably from about 2-about 40 wt. %, more preferably from about 8-about 30 wt. %, most preferably from about 15-about 25 wt. %, each relative to the weight of the oxidant preparation (M2).

A more preferred kit-of-parts as contemplated herein and a more preferred hair dyeing method as contemplated herein are each exemplified in that the oxidation preparation (M2) contains at least one tenside, selected from anion tensides and niotensides, as well as mixtures thereof, in a total quantity of from about 0.05-about 2 wt. %, preferably from about 0.3-about 1.5 wt. %, at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total quantity of from about 1-about 5 wt. %, preferably from about 1.5-about 4 wt. %, and at least one oil in a total quantity of from about 0.2-about 50 wt. %, preferably from about 2-about 40 wt. %, more preferably from about 8-about 30 wt. %, most preferably from about 15-about 25 wt. %, each relative to the weight of the oxidant preparation (M2), although no polymers having a polymerization degree of at least about 200 and no polymers having a molecular weight of about 10,000 Dalton or higher.

Anionic tensides suitable for the oxidant preparations as contemplated herein (M2) are all the anionic tensides discussed above for the agent as contemplated herein (M1).

Non-ionic tensides suitable for the oxidant preparations used as contemplated herein (M2) are all anionic surfactants, suitable for use on the human body, which have at least one non-ionic group that renders them water-soluble, more particularly a polyethylene glycol ether group having at least 2 ethylene oxide units, a glycoside group, more particularly a glucose or methyl glucose group, a poly glycoside group with an average of more than one glycoside unit, one polyglycerine group having at least two glycerine units, one sorbitan group, one amid group or several different of said groups, for example a sorbitan group and a polyethylene glycol ether group, and one lipophilic alkyl group having approximately 8 to about 30 C-atoms, preferably from 10 to about 24 C-atoms. The non-ionic tensides most preferably used are selected from, having from 7-about 80 mol of ethylene oxide per mol, ethoxylated castor oil, ethoxylated $C_8$-$C_{30}$ alkanols having from 4-about 100 mol ethylene oxide per mol, ethoxylated $C_8$-$C_{24}$ carbonic acid having from 5-about 30 mol of ethylene oxide per mol, having 4-about 50 mol of ethylene oxide per mol of sorbitan monoesters of linear saturated and unsaturated $C_{12}$-$C_{30}$ carbonic acids, which can be hydroxylated, more particularly those from myristiric acid, palmitic acid, stearic acid of mixtures of said fatty acids, alkylmono and oligoglycosides having from 8 to about 22 carbon atoms in the alkyl radical and the ethoxylated analogs thereof, as well as mixtures of the aforementioned substances.

The ethoxylated $C_8$-$C_{30}$ alkanols have the formula $R^1O(CH_2CH_2O)_nH$, wherein $R^1$ denotes a linear or branched alkyl and/or alkenyl radical having from 8-about 30 carbon atoms and n, the average number of ethylene oxide units per molecule, for integers from about 4-about 100, preferably from about 6-about 30, more preferably from about 12 to about 20 mol ethylene oxide to 1 mol alkanol, which is preferably selected from capryl alcohol, 2-ethylhexyl alcohol, caprin alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol, as well as the technical mixtures thereof. Adducts from 10-about 100 mol ethylene oxide on technical fat alcohols having from 12-18 carbon atoms, such as for example coco, palm, palm kernel or sebum fat alcohols are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, as well as Coceth-10, Coceth-12, Coceth-15, Coceth-20 and Coceth-30 are more preferred; Ceteth-10, Ceteth-12, Ceteth-15, Ceteth-20, Ceteth-30, Steareth-10, Steareth-12, Steareth-15, Steareth-20 and Steareth-30, as well as the mixtures thereof, are most preferred.

The ethoxylated $C_8$-$C_{30}$ carbonic acids have the formula $R^1O(CH_2CH_2O)_nH$, wherein $R^1O$ denotes a linear or branched, saturated or unsaturated acyl radical having from 8-30 carbon atoms and n, the average number of ethylene oxide units per molecule, for integers from 5-30, preferably from about 6-about 20, more preferably from about 6 to about 12 mol ethylene oxide to 1 mol $C_8$-$C_{30}$ carbonic acid, which is preferably selected from capryl alcohol, 2-ethylhexyl alcohol, caprin alcohol, lauric acid, isotridecaric acid, myristiric acid, cetyl acid, palmitoleic acid, stearic acid, isostearic acid, oleic acid, elaidic acid, petroselic acid, arachine acid, gadoleic acid, behenic acid, erucic acid and brassidic acid, as well as the technical mixtures thereof. Adducts from 5-about 30, preferably from 6-about 20, more preferably from 6 to 12 mol of ethylene oxide on technical fatty acids having from 12-18 carbon atoms, such as coco, palm, palm kernel or sebum fat alcohols are also suitable.

With respect to the cosmetic agent (M1) in container $C_1$ and the oxidant preparation (M2) in container $C_2$ of the kit as contemplated herein and preferred as contemplated herein, the statements made about the agents as contemplated herein and preferred as contemplated herein apply mutatis mutandis.

With respect to the cosmetic agent (M1) in container $C_1$ and the method for oxidative hair dyeing as contemplated herein and preferred as contemplated herein, the statements made about the agents as contemplated herein and preferred as contemplated herein apply mutatis mutandis.

With respect to oxidant preparation (M2) in container $C_1$ and the method for oxidative hair dyeing as contemplated herein and preferred as contemplated herein, the statements made about the oxidant preparations (M2) of the kits as contemplated herein and preferred as contemplated herein apply mutatis mutandis.

The subject matter of the present disclosure is summarized as follows:

1. Agent for oxidative hair dyeing containing, relative to the weight of the agent in each case,
   from about 70 to about 95 wt. % water,
   at least one oxidation dye precursor,
   at least one alkalizing agent,
   at least one tenside, selected from anionic, zwitterionic and amphoteric tensides, as well as mixtures thereof, in a total quantity of from about 0.1-about 2 wt. %,
   Sodium polyacrylate in a total quantity of from about 0.1-about 1.5 wt. %, preferably from about 0.5-about 1.3 wt. %, most preferably from about 0.8-about 1.1 wt. %,
   at least one linear, saturated alkanol with two or three hydroxy groups and from 2 to 8 carbon atoms in the alkyl group in a total quantity of from about 0-about 3 wt. %, wherein
   no saturated or unsaturated non-alkoxylated alkanols with a hydroxy group and from 1 to about 50 carbon atoms in the alk(en)yl group and
   no saturated or unsaturated alkanecarboxylic acids with from 1 to about 50 carbon atoms, and
   no oxidants
   are included in the agent.

2. Agent according to Item 1, exemplified in that the alkalizing agent is selected from the group comprising ammonium hydroxide, basic amino acids, alkalihydroxides, alkanolamines, alkali metal metasilicates, alkali phosphates and alkali hydrogen phosphates, as well as the mixtures thereof.

3. Agent according to Items 1 or 2, exemplified in that the at least one anionic or zwitterionic tenside is selected from $C_8$-$C_{20}$ alkyl sulphates, $C_8$-$C_{20}$-alkyl ether sulfphates and $C_8$-$C_{20}$ ether carboxylic acids, each with from 8 to about 20 C-atoms in the alkyl group and from 0 to 12 ethylene oxide groups in the molecule, wherein sodium laureth(2)sulphate is particularly preferred, moreover from coco-acylaminopropyl-dimethyl ammonium glycinate, as well as from mixtures of said tensides, wherein preferably at least one anion or zwitteriontenside is contained in a total quantity of from about 0.3-about 1.5 wt. %, preferably from about 0.5-about 1.2 wt. %, relative to the weight of the agent in each case.

4. Agent according to one of Items 1-3, exemplified in that sodium polyacrylate has an average molecular weight Mw in the range from about 1,000,000 to about 20,000,000 Dalton, preferably from about 6,000,000 to about 15,000,000 Dalton.

5. Agent according to one of Items 1-4, exemplified in that sodium polyacrylate is used pregelled in a water-in-oil emulsion.

6. Agent according to one of Item 5, exemplified in that said water-in-oil emulsion, contains, relative to the weight thereof in each case, from about 40-about 60 wt. % sodium polyacrylate, from about 25-about 45 wt. % oil(s) in total, preferably mineral oil, from about 0.5-about 4.9 wt. % tenside(s) in total, preferably from about 0.5-about 4.9 wt. % niotenside(s), and from about 0.5-about 4.9 wt. % water.

7. Agent according to one of Items 1-6, exemplified by a viscosity in the range of from about 10,000-about 75,000 mPas, preferably from about 12,000-about 60,000 mPas, more preferably from about 13,000-about 50,000 mPas, most preferably from about 15,000-about 25,000 mPas, in each case measured at 20° C. by employing a Brookfield rotational viscometer at a rotational frequency of 4 rpm with Spindle 5.

8. Agent according to one of claims 1-7, exemplified by a pH value in the range of from about 8-about 12, preferably from about 9-about 11.5, more preferably from about 9.5-about 10.5, in each case measured at 20° C.

9. Agent according to one of Items 1-8, exemplified in that at least one cross-linked copolymer from acrylic acid and non-ethoxylated esters of the acrylic acid with linear C10-C30 mono-alcohols is contained, which is preferably selected from copolymers having the INCI trade name Acrylates/C10-30 Alkyl Acrylate Crosspolymer.

10. Agent according to Item 9, exemplified in that at least one cross-linked copolymer from acrylic acid and non-ethoxylated esters of the acrylic acid with linear C10-C30 mono-alcohols are contained in a total quantity of from about 0.05-about 2 wt. %, preferably from about 0.1-about 1.5 wt. %, more preferably from about 0.3-about 1 wt. %, most preferably from about 0.5-about 0.8 wt. %, in each case relative to the weight of the agent.

11. Agent according to one of Items 1-10, exemplified in that, relative to their weight, polyethylenglycol(s) having an average molecular weight of from about 100 to about 100,000 g·mol$^{-1}$ in a total quantity of from about 0-about 0.2 wt. %, preferably from about 0-about 0.1 wt. % are contained.

12. Agent according to one of Items 1-11, exemplified in that fatty substances having a melting point of about 30° C. and above at 1013 mbar and a water-solubility of about 0.005 wt. % and below in a total quantity of from about 0-about 0.1 wt. %, preferably 0 wt. %, relative to the weight of the agent, are contained.

13. Kit-of-parts comprising—packaged separately from one another—
a) at least one container (C1), containing a cosmetic agent according to one of claims 1 to 12, and
b) at least one container (C2), containing an oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and which has a pH value in the range from about 2.0 to about 6.5, preferably from about 2.5-about 5.5, more preferably from about 2.8 to about 5.0, in each case measured at 20° C., wherein each of the wt. % values are relative to the weight of the oxidant preparation (M2).

14. Kit-of-parts according to Item 13, exemplified in that the oxidant preparation (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2).

15. Kit-of-parts according to Item 14, exemplified in that the oxidant preparation (M2) contains no polymer with a polymerization degree of at least about 200 and no polymer with a molecular weight of about 10000 Dalton or higher.

16. Kit-of-parts according to Item 13, exemplified in that the oxidant preparation (M2) contains at least one copolymer, selected from cross-linked acrylic acid/acrylic acid —C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cation tenside.

17. Method for oxidative hair dyeing, comprising the following method steps:
i) Providing a cosmetic agent (M1) according to one of the items 1 to 12,
ii) Providing an oxidant preparation (M2), which contains from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and which has a pH value in the range from about 2.0 to about 6.5, preferably from about 2.5-about 5.5, more preferably from about 2.8 to about 5.0, in each case measured at 20° C., wherein each of the wt. % values are relative to the weight of the oxidant preparation (M2), wherein optionally, either at least one cation tenside or at least one copolymer, selected from cross-linked acrylic acid/acrylic acid-C1-C6-alkyl ester-copolymers and cross-linked methacrylic acid/acrylic acid-C1-C6-alkyl ester-copolymers is contained.
iii) Mixing the cosmetic agent (M1) with the oxidant preparation (M2), preferably in a weight ratio (M1):(M2) in the range from about 1:0.8 t about o 1:2.5, preferably from about 1:1 to about 1:2, immediately afterwards
iv) Applying the mixture obtained in Step iii) onto the hair and leaving said mixture for a period of from about 1 to about 60 minutes, preferably from about 20 to about 45 minutes at room temperature and/or at from about 30-about 60° C., preferably at from about 32-about 50° C. on the hair,
v) Rinsing the hair with water and/or a cleansing composition, and
vi) where necessary, applying a post-treatment agent onto the hair and, where necessary, rinsing out, then drying.

18. Method for oxidative hair dyeing according to Item 17, exemplified in that the oxidant preparation (M2) contains at least one cation tenside, preferably in a total quantity of from about 0.05-about 3 wt. %, more preferably from about 0.1-about 1.5 wt. %, most preferably from about 0.3-about 0.9 wt. %, in each case relative to the weight of the oxidant preparation (M2), and contains no polymer with a polymerization degree of at least about 200 and no polymer with a molecular weight of about 10000 Dalton or higher.

19. Method for oxidative hair dyeing according to Item 17, exemplified in that the oxidant preparation (M2) contains at least one copolymer, selected from cross-linked acrylic acid/acrylic acid —C1-C6 alkyl ester-copolymers and cross-linked methacrylic acid/acrylic acid-C1-C6-alkyl ester copolymers, preferably in a total quantity of from about 0.1-about 7 wt. %, more preferably from about 0.5-about 6 wt. %, most preferably from about 1-about 4.5 wt. %, in each case relative to the weight of the oxidant preparation (M2), and preferably contains no cation tenside.

20. Method for oxidative hair dyeing, comprising the following method steps:

i) Providing a cosmetic agent (M1) according to one of the items 1 to 12, ii) Providing an oxidant preparation (M2), containing from about 40-about 96 wt. %, preferably from about 70-about 93 wt. %, more preferably from about 80-about 90 wt. % of water, also hydrogen peroxide in a total quantity of from about 0.5 to about 23 wt. %, preferably from about 2.5 to about 21 wt. %, more preferably from about 4 to about 20 wt. %, even more preferably from about 5 to about 18 wt. % and most preferably from about 6 to about 12 wt. %, and a pH value in the range from about 2.0 to about 6.5, preferably from about 2.5-about 5.5, most preferably from about 2.8 to about 5.0, having, in each case measured at 20° C., wherein preferably at least one tenside, selected from anion tensides and niotensides, as well as mixtures thereof, in a total quantity from about 0.05-about 2 wt. %, preferably from about 0.3-about 1.5 wt. %, and at least one linear, saturated 1-alkanol having from 14 to about 22 carbon atoms, selected from 1-tetradecanol (myristyl alcohol), 1-hexadecanol (cetyl alcohol), 1-octadecanol (stearyl alcohol) and 1-eicosanol (arachyl alcohol) as well as mixtures thereof, in a total quantity from about 1-about 5 wt. %, preferably from about 1.5-about 4 wt. %, wherein optionally at least one oil in a total quantity of from about 0.2-about 50 wt. %, preferably from about 2-about 40 wt. %, more preferably from about 8-about 30 wt. %, most preferably from about 15-about 25 wt. %, and/or optionally at least one cation tenside, preferably in a total quantity of from about 0.05-about 3 wt. %, more preferably from about 0.1-about 1.5 wt. %, most preferably from about 0.3-about 0.9 wt. %, is contained, wherein all quantity data are relative to the weight of the oxidant preparation (M2), iii) Mixing the cosmetic agent (M1) with the oxidant preparation (M2), preferably in a weight ratio (M1):(M2) in the range from about 1:0.8 to about 1:2.5, preferably from about 1:1 to about 1:2, immediately afterwards iv) Applying the mixture obtained in Step iii) onto the hair and leaving said mixture for a period of from about 1 to about 60 minutes, preferably from about 20 to about 45 minutes at room temperature and/or at from about 30-about 60° C., v) Rinsing the hair with water and/or a cleansing composition, and vi) where necessary, applying a post-treatment agent onto the hair and, where necessary, rinsing out, then drying.

The following examples are intended to explain the subject matter of the present disclosure without having any limiting effect.

EXAMPLES

TABLE 1

Dye gel for oxidative hair dyeing

| Ingredient | Test sample (wt. %) |
| --- | --- |
| Monoethanolamine (2-aminoethan-1-ol) | 0.40 |
| Ammonium hydroxide | 4.63 |
| Acrylates/C10-30 Alkyl Acrylate Crosspolymer | 0.40 |
| Sodium polyacrylate* | (active content) 1.00 |
| Mineral oil | 0.70 |
| Trideceth-6 | 0.10 |
| Sodium laureth sulphate | 0.80 |
| L-Serin | 0.75 |

TABLE 1-continued

Dye gel for oxidative hair dyeing

| Ingredient | Test sample (wt. %) |
| --- | --- |
| Sodium sulfate | 0.30 |
| Tetranatrium EDTA | 0.30 |
| Ascorbic acid | 0.08 |
| Toluen-2,5-diaminsulphate | 1.35 |
| Resorcin | 0.44 |
| 2-Methyl resorcin | 0.10 |
| m-aminophenol | 0.06 |
| 4-chlororesorcin | 0.06 |
| 2-amino-3-methylphenol | 0.05 |
| Water | ad 100.00 |

*Sodium polyacrylate, pregelled in a water-in-mineral oil emulsion with Trideceth-6 as the emulsifier Viscosity: 15,000 mPas, measured at 20° C. by employing a Brookfield rotational viscometer at a rotational frequency of 4 rpm with Spindle 5

TABLE 2

Oxidant-containing developer for the dye creme gel from Table 1

| Ingredient | Test sample (wt. %) |
| --- | --- |
| Sodium benzoate | 0.04 |
| Dipicolinic acid (2,6-dicarboxypyridin) | 0.10 |
| Di-sodium pyrophosphate | 0.10 |
| Potassium hydroxide | 0.10 |
| 1,2-Propanediol | 1.00 |
| Etidronic acid | 0.15 |
| Paraffin oil | 0.30 |
| Stearyl trimethyl ammonium chloride | 0.30 |
| Cetearyl alcohol | 3.40 |
| Ceteareth-20 | 1.00 |
| Hydrogen peroxide | 6.00 |
| Water | ad 100.00 |

Viscosity: 4.500 mPas, measured at 20° C. with a rotational viscometer Haake VT 550 at a rotational frequency of 4 rpm with measurement geometry MV II

TABLE 3

Oxidant-containing developer for the dye creme gel from Table 1

| Ingredient | Test sample (wt. %) |
| --- | --- |
| Sodium hydroxide | 0.40 |
| Dipicolinic acid (2,6-dicarboxypyridin) | 0.10 |
| Di-sodium pyrophosphate | 0.03 |
| Etidronic acid | 0.15 |
| Mixture of cross-linked (meth)acrylic acid/ acrylic acid -C1-C6-alkyl ester copolymers (ex Aculyn 33A) | 4.20 |
| Sodium laureth(2)sulphate | 0.50 |
| Hydrogen peroxide | 6.00 |
| Water | ad 100.00 |

* Aculyn 33A: hydrous dispersion of Acrylates Copolymer (mixture of cross-linked (meth)acrylic acid/acrylic acid —C1-C6-alkyl ester copolymers); 28 wt. % polymer content (active substance)

Viscosity: * Viscosity: measured at 20° C. by employing a Brookfield rotational viscometer at a rotational frequency of 20 rpm with Spindle 2

Production of the Application Mixtures and Coloration on Hair

Dye gel and developer according to Table 4 were mixed with one another in a homogeneous manner. The application mixtures thus obtained were applied, immediately after production, to human hair (natural white hair, Kerling) (liquor ratio 4 gram application mixture per gram of hair and left on the hair for 30 minutes at room temperature (22° C.). The strands were then rinsed out and towel-dried.

TABLE 4

Production of the application mixtures for coloration on hair

| Dye gel (M1) (agent as contemplated herein) | Developer (M2) | Weight ratio (M1):(M2) | Viscosity of the application mixture [mPas]* |
|---|---|---|---|
| according to Table 1 | according to Table 2 | 1:2 | 56,000 |
| according to Table 1 | according to Table 2 | 1:1 | 47,000 |
| according to Table 1 | according to Table 3 | 1:2 | 23,000 |
| according to Table 1 | according to Table 3 | 1:1 | 22,000 |

*Viscosity: measured at 20° C. by employing a Brookfield rotational viscometer at a rotational frequency of 4 rpm with Spindle 5.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Agent for oxidative hair dyeing comprising, relative to the weight of the agent,
   from about 70 to about 95 wt. % water,
   at least one oxidation dye precursor,
   at least one alkalizing agent,
   at least one tenside, selected from anionic, zwitterionic, amphoteric tensides, or mixtures thereof, in a total quantity of from about 0.1-about 2 wt. %,
   Sodium polyacrylate in a total quantity of from about 0.1-about 1.5 wt. %,
   at least one linear, saturated alkanol with two or three hydroxy groups and from about 2 to about 8 carbon atoms in the alkyl group in a total quantity of from 0-about 3 wt. %,
   wherein
   no saturated or unsaturated non-alkoxylated alkanols with a hydroxy group and from about 1 to about 50 carbon atoms in the alk(en)yl group and
   no saturated or unsaturated alkanecarboxylic acids with from about 1 to about 50 carbon atoms, and
   no oxidants
   are included in the agent.

2. Agent according to claim 1, wherein the alkalizing agent is selected from ammonium hydroxide, basic amino acids, alkalihydroxides, alkanolamines, alkali metal meta-silicates, alkali phosphates, alkali hydrogen phosphates, or mixtures thereof.

3. Agent according to claim 1, wherein the at least one anionic or zwitterionic tenside is present and is selected from $C_8$-$C_{20}$ alkyl sulphates, $C_8$-$C_{20}$-alkyl ether sulfphates and $C_8$-$C_{20}$ ether carboxylic acids, each with from about 8 to about 20 C-atoms in the alkyl group and from 0 to about 12 ethylene oxide groups in the molecule, coco-acylaminopropyl-dimethyl ammonium glycinate, or mixtures thereof.

4. Agent according to claim 1, wherein the agent includes a water-in-oil emulsion and the sodium polyacrylate is pregelled in said water-in-oil emulsion, wherein said water-in-oil emulsion comprises, relative to the weight of said water-in-oil emulsion the sodium polyacrylate, from about 25-about 45 wt. % oil(s), from about 0.5-about 4.9 wt. % tenside(s), and from about 0.5-about 4.9 wt. % water.

5. Agent according to claim 1, having a viscosity in the range of from about 10,000-about 75,000 mPas, measured at 20° C. by employing a Brookfield rotational viscometer at a rotational frequency of 4 rpm with Spindle 5.

6. Agent according to claim 1, having a pH value in the range of from about 8-about 12, measured at 20° C.

7. Agent according to claim 1, further comprising at least one cross-linked copolymer chosen from acrylic acid and non-ethoxylated esters of acrylic acid with linear C10-C30 mono-alcohols.

8. Kit-of-parts comprising—packaged separately from one another—
   a) at least one container (C1), comprising an agent for oxidative hair dyeing according to claim 1, and
   b) at least one container (C2), comprising an oxidant preparation (M2), which comprises from about 40-about 96 wt. % of water, also hydrogen peroxide in a total quantity of from about 0.5 to about 23 wt. %, and which has a pH value in the range from about 2.0 to about 6.5, measured at 20° C., wherein each of the wt. % values are relative to the weight of the oxidant preparation (M2).

9. Kit-of-parts according to claim 8, wherein the oxidant preparation (M2) comprises at least one cation tenside.

10. Kit-of-parts according to claim 9, wherein the oxidant preparation (M2) comprises no polymer with a polymerization degree of at least about 200 and no polymer with a molecular weight of about 10000 Dalton or higher.

11. Kit-of-parts according to claim 8, wherein the oxidant preparation (M2) comprises at least one copolymer, selected from cross-linked acrylic acid/acrylic acid —C1-C6 alkyl ester-copolymers and cross-linked methacrylic acid/acrylic acid-C1-C6-alkyl ester copolymers.

12. Method for oxidative hair dyeing, comprising the following method steps:
   i) Providing a cosmetic agent (M1) for oxidative hair dyeing according to claim 1,
   ii) Providing an oxidant preparation (M2), which comprises from about 40-about 96 wt. % of water, hydrogen peroxide in a total quantity of from about 0.5 to about 23 wt. %, and which has a pH value in the range from about 2.0 to about 6.5, measured at 20° C., wherein each of the wt. % values are relative to the weight of the oxidant preparation (M2), wherein optionally, either at least one cation tenside or at least one copolymer, selected from cross-linked acrylic acid/acrylic acid-C1-C6-alkyl ester-copolymers and cross-linked methacrylic acid/acrylic acid-C1-C6-alkyl ester-copolymers is included,
   iii) Mixing the cosmetic agent (M1) with the oxidant preparation (M2), immediately afterwards,
   iv) Applying the mixture obtained in Step iii) onto the hair and leaving said mixture for a period of from about 1 to about 60 minutes, at room temperature or at from about 30-about 60° C. on the hair,
   v) Rinsing the hair with water and/or a cleansing composition, and vi) optionally, applying a post-treatment agent onto the hair and, optionally, rinsing out, then drying.

13. Method for oxidative hair dyeing according to claim 12, wherein the oxidant preparation (M2) comprises at least one cation tenside, and comprises no polymer with a polymerization degree of at least about 200 and no polymer with a molecular weight of about 10000 Dalton or higher.

14. Method for oxidative hair dyeing according to claim 12, wherein the oxidant preparation (M2) comprises at least one copolymer, selected from cross-linked acrylic acid/ acrylic acid —C1-C6 alkyl ester-copolymers and cross-linked methacrylic acid/acrylic acid-C1-C6-alkyl ester copolymers.

15. Method for oxidative hair dyeing according to claim 12, wherein the oxidant preparation (M2) comprises at least one tenside, selected from anion tensides, non-ionic tensides, or mixtures thereof, in a total quantity of from about 0.05-about 2 wt. %, and at least one linear, saturated 1-alkanol with from about 14 to about 22 carbon atoms, selected from 1-tetradecanol (myristyl alcohol), 1-hexadecanol (cetyl alcohol), 1-octadecanol (stearyl alcohol), 1-eicosanol (arachyl alcohol), or mixtures thereof, in a total quantity of from about 1-about 5 wt. %, wherein optionally, at least one oil is included in a total quantity of from about 0.2-about 50 wt. %, and/or optionally at least one cation tenside, wherein all quantity values are relative to the weight of the oxidant preparation (M2).

16. Agent according to claim 1, wherein the sodium polyacrylate has an average molecular weight Mw in the range from about 1,000,000 to about 20,000,000 Dalton.

17. Agent according to claim 3, wherein the at least one anionic or zwitterionic tenside is present and includes sodium laureth(2)sulphate.

18. Agent according to claim 3, wherein the at least one anion or zwitterion tenside is included in a total quantity of from about 0.3-about 1.5 wt. %, relative to the weight of the agent.

19. Agent according to claim 7, wherein the at least one cross-linked copolymer is present in a total quantity of from about 0.05-about 2 wt. %, relative to the weight of the agent.

20. Agent according to claim 1, wherein:
the at least one anionic or zwitterionic tenside is selected from $C_8$-$C_{20}$ alkyl sulphates, $C_8$-$C_{20}$-alkyl ether sulfphates and $C_8$-$C_{20}$ ether carboxylic acids, each with from about 8 to about 20 C-atoms in the alkyl group and from 0 to about 12 ethylene oxide groups in the molecule,
the at least one anion or zwitterion tenside is included in a total quantity of from about 0.3-about 1.5 wt. %, relative to the weight of the agent, and
the agent further comprises at least one cross-linked copolymer chosen from acrylic acid and non-ethoxylated esters of acrylic acid with linear C10-C30 monoalcohols present in a total quantity of from about 0.05-about 2 wt. %, relative to the weight of the agent.

* * * * *